US008317676B2

(12) United States Patent
Widenhouse et al.

(10) Patent No.: US 8,317,676 B2
(45) Date of Patent: Nov. 27, 2012

(54) GASTRIC BAND WITH CONTRASTING SUPPLY TUBE

(75) Inventors: Christopher W. Widenhouse, Clarksville, OH (US); Kevin R. Doll, Mason, OH (US); Lauren S. Weaneer, Beavercreek, OH (US); Jeffrey P. Wiley, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 961 days.

(21) Appl. No.: 11/798,497

(22) Filed: May 14, 2007

(65) Prior Publication Data

US 2008/0287974 A1 Nov. 20, 2008

(51) Int. Cl.
*A61F 2/00* (2006.01)
(52) U.S. Cl. .......................................... 600/37; 604/909
(58) Field of Classification Search .............. 600/29–32, 600/37; 604/909
See application file for complete search history.

(56) References Cited

U.S. PATENT DOCUMENTS

| 4,634,443 | A | * | 1/1987 | Haber | 600/31 |
| 5,630,806 | A | * | 5/1997 | Inagaki et al. | 604/524 |
| 6,099,506 | A | * | 8/2000 | Macoviak et al. | 604/173 |
| 2002/0198548 | A1 | * | 12/2002 | Robert | 606/157 |
| 2005/0043751 | A1 | * | 2/2005 | Phan et al. | 606/155 |
| 2005/0055039 | A1 | * | 3/2005 | Burnett et al. | 606/151 |
| 2007/0250020 | A1 | * | 10/2007 | Kim et al. | 604/264 |

* cited by examiner

*Primary Examiner* — Charles A Marmor, II
*Assistant Examiner* — Carrie R Dorna
(74) *Attorney, Agent, or Firm* — Welsh Flaxman & Gitler LLC

(57) ABSTRACT

A balloon-type gastric band includes a balloon shaped and dimensioned to circumscribe a stomach at a predetermined location. A supply tube is secured to the balloon for fluid communication with an internal cavity of the balloon, wherein the supply tube includes both at least one colored section and at least one clear section for respectively contrasting the supply tube from surrounding tissue when placed within a patient and facilitating identification of leaks within the supply tube. In accordance with an alternate embodiment the supply tube is colored while remaining translucent.

13 Claims, 4 Drawing Sheets

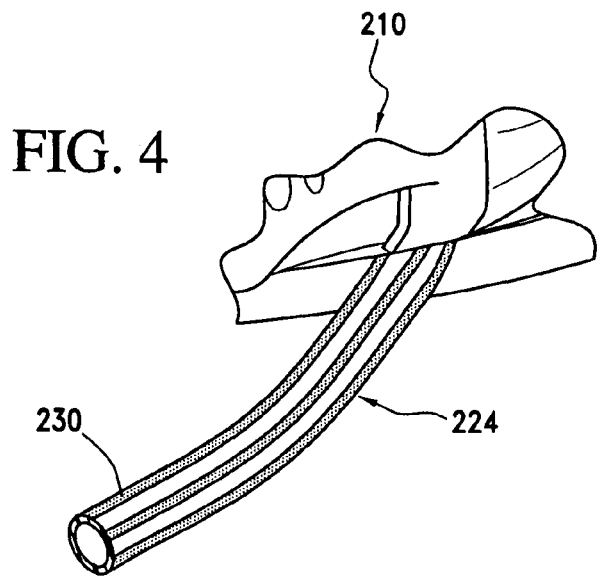
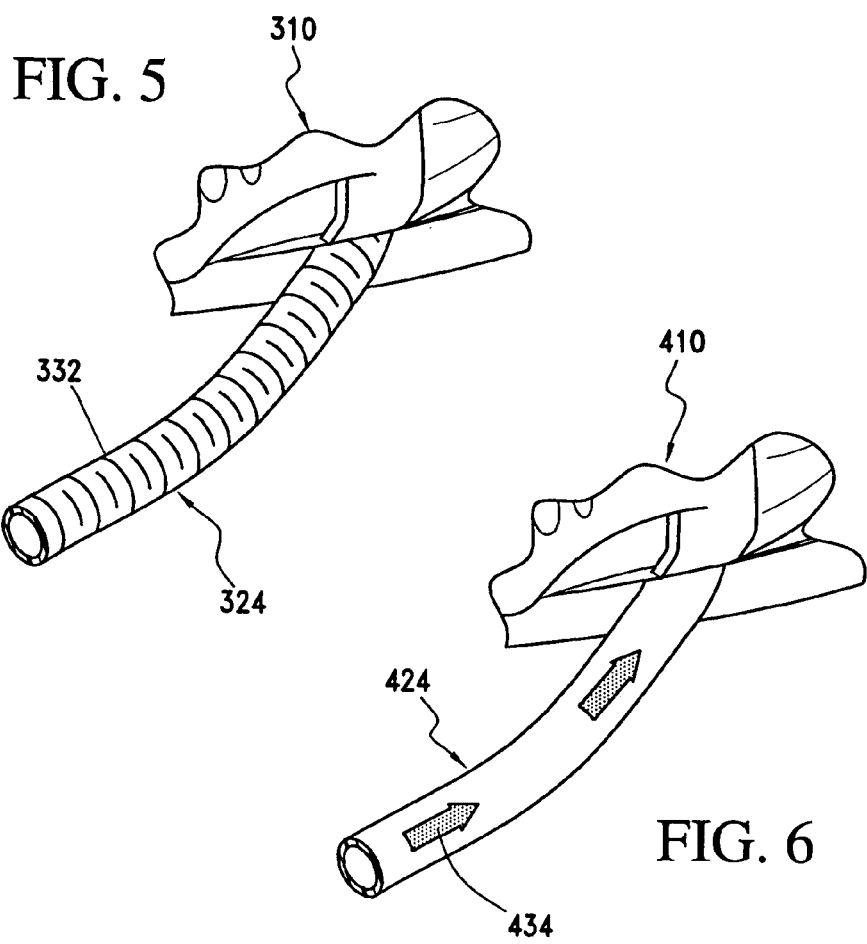

GASTRIC BAND WITH CONTRASTING SUPPLY TUBE

BACKGROUND OF THE INVENTION

1. Field of the Invention

The invention relates to a gastric band with a supply tube that includes radiopaque and clear characteristics.

2. Description of the Related Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of one hundred billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. Other forms of bariatric surgery include Fobi pouch, bilio-pancreatic diversion, and gastroplastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is one of these methods. Gastric-banding is a type of gastric reduction surgery attempting to limit food intake by reducing the size of the stomach. In contrast to RYGB and other stomach reduction procedures, gastric-banding does not require the alteration of the anatomy of the digestive tract in the duodenum or jejunum.

Since the early 1980's, gastric bands have provided an effective alternative to gastric bypass and other irreversible surgical weight loss treatments for the morbidly obese. Several alternate procedures are performed under the heading of gastric-banding. Some banding techniques employ a gastric ring, others use a band, some use stomach staples and still other procedures use a combination of rings, bands and staples. Among the procedures most commonly performed are vertical banded gastroplasty (VBG), silastic ring gastroplasty (SRG) and adjustable silastic gastric banding (AGB).

In general, the gastric band is wrapped around an upper portion of the patient's stomach, forming a stoma that is less than the normal interior diameter of the stomach. This restricts food passing from an upper portion to a lower digestive portion of the stomach. When the stoma is of an appropriate size, food held in the upper portion of the stomach provides a feeling of fullness that discourages over eating.

More particularly, and in practice, the gastric band is inserted behind the stomach and the ends of the gastric band are coupled to latch the device about the stomach. It is often difficult to visualize the gastric band both during the gastric band application procedure and after the procedure has been completed. As such, a need exists for mechanisms to improve one's ability to visualize a gastric band. The present invention provides such a mechanism.

SUMMARY OF THE INVENTION

It is, therefore, an object of the present invention to provide a balloon-type gastric band including a balloon shaped and dimensioned to circumscribe a stomach at a predetermined location. A supply tube is secured to the balloon for fluid communication with an internal cavity of the balloon, wherein the supply tube includes both at least one colored section and at least one clear section for respectively contrasting the supply tube from surrounding tissue when placed within a patient and facilitating identification of leaks within the supply tube.

It is also an object of the present invention to provide a balloon-type gastric band wherein the at least one colored section is an arrow.

It is also another object of the present invention to provide a balloon-type gastric band wherein the at least one colored section is text.

It is also a further object of the present invention to provide a balloon-type gastric band wherein the at least one colored section includes gradations along a length of the supply tube.

It is another object of the present invention to provide a balloon-type gastric band wherein the at least one colored section is radiopaque.

It is a further an object of the present invention to provide a balloon-type gastric band wherein the at least one colored section is spiraled.

It is also an object of the present invention to provide a balloon-type gastric band wherein the at least one colored section is striped.

It is still another object of the present invention to provide a balloon-type gastric band wherein the at least one colored section is a circumferential stripe.

It is yet another object of the present invention to provide a balloon-type gastric band wherein the at least one colored section is a longitudinal stripe.

It is also an object of the present invention to provide a balloon-type gastric band wherein the at least one colored section is a colored pad print.

It is another object of the present invention to provide a balloon-type gastric band including a balloon shaped and dimensioned to circumscribe a stomach at a predetermined location. A supply tube is secured to the balloon for fluid communication with an internal cavity of the balloon, wherein the supply tube is colored while remaining translucent.

It is a further object of the present invention to provide a balloon-type gastric band wherein the supply tube includes a contrast agent incorporated therein.

It is also an object of the present invention to provide a balloon-type gastric band wherein the contrast agent is radiopaque.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 3, 4, 5, 6, 7 and 8 are detailed views showing various embodiments in accordance with the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
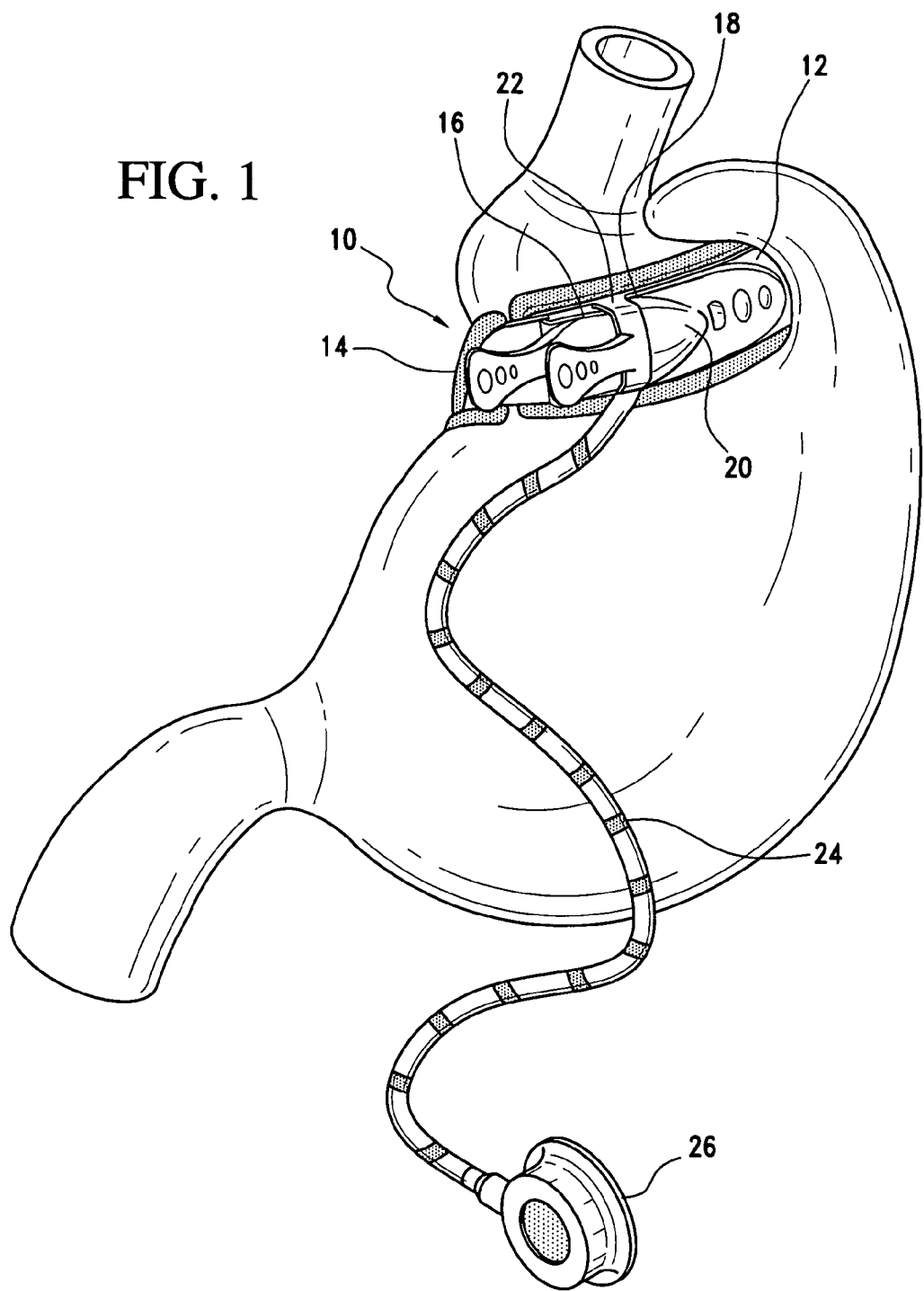
FIG. 1 is a perspective view of a gastric band in accordance with a preferred embodiment of the present invention secured about the stomach of a patient at a predetermined location.
Figure 2:
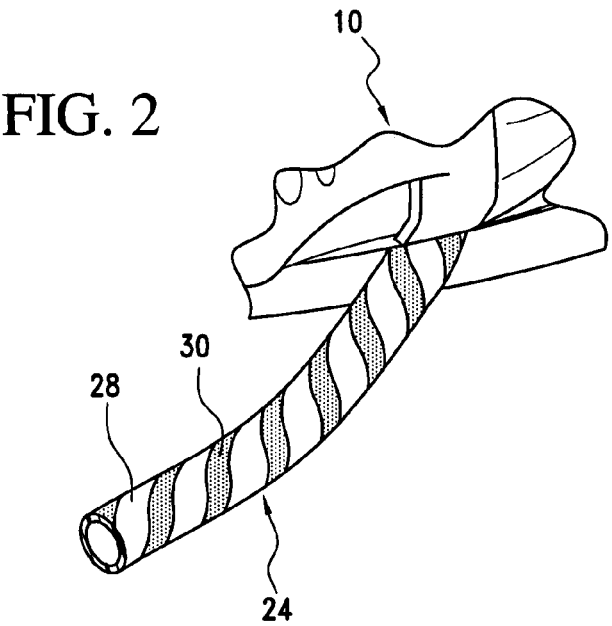
FIG. 2 is a detailed view of the supply tube shown in FIG. 1.

Referring to FIGS. 1 and 2, a balloon-type gastric band 10 is disclosed in accordance with a preferred embodiment of the present invention. The gastric band 10 is generally composed of a reinforcing belt 12 to which an elongated balloon 14 is secured. The belt 12 includes a first end 16 and a second end 18 to which first and second latching members 20, 22 are respectively secured. In accordance with a preferred embodiment the first and second latching members 20, 22 are shaped and dimensioned for selective engagement, and are the same as disclosed in commonly owned U.S. patent application Ser. No. 11/182,072, entitled "Latching Device for Gastric Band", filed Jul. 15, 2005, which is incorporated herein by reference.

In accordance with a preferred embodiment, the belt 12 and balloon 14 are constructed as disclosed in commonly owned U.S. patent application Ser. No. 11/364,361, filed Mar. 1, 2006, entitled "Gastric Band", which is incorporated herein by reference. As such, the balloon 14 and belt 12 are respectively coupled by either overmolding or separate molding with subsequent adhesive bonding.

Regardless of how the gastric band 10 is molded or assembled together, the belt 12 and balloon 14 components may consist of the same materials or different materials (material durometer, fillers such as $BaSO_4$, $TiO_2$, colorants, etc.). In addition, features within the component (for example, the first and second latching members of the latching assembly) may vary in composition. These features may be adhered to the rest of the product with adhesive, mechanical fastening (i.e., snap fits), welding, co-molding, or overmolding.

The balloon 14 includes a longitudinally extending body and is constructed to enhance contact with the stomach wall when applied thereto. With this in mind, the balloon is constructed as a precurved, low pressure, high volume balloon. The balloon is constructed to maintain a soft and flexible surface (low pressure) when applied to the stomach tissue. The balloon is also constructed to provide 360 degree coverage to prevent tissue pinching or discontinuities in stomach shape, and, as such, may employ the balloon construction disclosed in commonly owned U.S. patent application Ser. No. 11/182,070, entitled "GASTRIC BAND WITH MATING END PROFILES", filed Jul. 15, 2005, which is incorporated herein by reference. The balloon is further constructed such that it reaches its fully inflated and encircling configuration with minimal "folds". In addition, the balloon is constructed to exhibit no folds or creases (single axis, not dual axis) when all fluid is evacuated therefrom.

As those skilled in the art will certainly appreciate, a supply tube 24 is used to connect the internal cavity of the balloon 14 of the gastric band 10 with a fluid injection port 26, for example, velocity port. The utilization of the supply tube 24 with a remote fluid injection port 26 allows for controlled inflation and deflation of the balloon 14 in a predetermined manner. The exact position of the supply tube 24 is important in that the surgeon does not want the supply tube 24 to be a visual obstruction during locking and/or other manipulation of the gastric band 10. In addition, once placement of the gastric band 10 is complete, the supply tube 24 should not cause irritation to surrounding tissue (for example, sticking directly into the liver or spleen). Surgeons also do not want to pull the supply tube 24 through a retro-gastric tunnel, since they cannot easily see if the tissue is being damaged. The tube should also be able to act as a safe grasping location for manipulation of the gastric band 10, the supply tube 24 must not kink at the junction to the gastric band 10 and prevent fluid flow, and the supply tube 24 location should facilitate passage of the band through a small trocar.

In accordance with various preferred embodiments of the present invention, different tube placements may be employed as disclosed in commonly owned U.S. patent application Ser. No. 11/364,362, entitled "Gastric Band", filed Mar. 1, 2006 and Ser. No. 11/364,363, entitled "Precurved Gastric Band", filed Mar. 1, 2006, which are incorporated herein by reference.

Regardless of which supply tube construction is employed in accordance with the present invention, it is necessary that the gastric band 10 be connected with a remote fluid injection port 26 employed as an injection site for controlling the application of fluid for filling the balloon 14. In accordance with a preferred embodiment of the present invention, the supply tube 24 is composed of the silicone or other biocompatible polymers, and includes a contrast mechanism enhancing visualization of the supply tube 24 both during the procedure and postoperatively through the implementation of radiopaque agents while maintaining clear sections 28 (or translucent characteristics as discussed below in accordance with an alternate embodiment discussed below) for the observation of leaks or bubbles during application. It is the primary intent of the present invention to provide for visualization of the supply tube 24 relative to the fluid injection port 26 (postoperatively) and relative to the tissue (during the procedure). In addition, the inclusion of annotations on the supply tube 24, for example, arrows 334 as shown in FIG. 5 and discussed below, also provides for contrast with the belt 12 and/or balloon 14 by showing a direction of the supply tube 24 relative to the belt 12 and/or balloon 14. More particularly, and in accordance with this embodiment, the contrast mechanism is achieved by providing the supply tube 24 with both visually clear sections 28 and radiopaque, white colored sections 30. In accordance with this embodiment, the clear sections 28 and the radiopaque, white colored sections 30 are spiraled.

The clear sections 28 are relatively transparent portions of the supply tube 24 that allow the medical practitioner to check for leaks or air bubbles in the supply tube 24 during the procedure in a traditional manner. As those skilled in the art will appreciate, the clear sections 28 may vary in their transparency but will ultimately be sufficiently transparent to allow a medical practitioner to monitor the internal structure of the supply tube 24 for leaks in a traditional manner.

The radiopaque, white colored sections 30 are used postoperatively as a non-invasive diagnostic tool (for evaluating either leaks in the supply tube 24 or whether the supply tube 24 and remote fluid injection port 26 are still connected). The colored sections 30 also allow for improved visualization during the procedure. Although white, colored sections are disclosed herein in accordance with a preferred embodiment of the present invention, those skilled in the art will appreciate the colored sections may take on a variety of colors and hues without departing from the spirit of the invention. In general, however, the specific color chosen for use in accordance with various applications should be chosen to enhance visualization, whether that visualization be postoperative visualization by means of an external diagnostic tool or actual visualization of the supply tube 24 during the surgical procedure.

In accordance with a preferred embodiment of the present invention, the radiopaque, white colored sections 30 may be created by several different radiopaque (and non-radiopaque) contrast agents, such as, $BaSO_4$, $TiO_2$ or Ta. While the use of the radiopaque agents provides for remote visualization (for example, postoperatively), the non-radiopaque agents enhance visualization by relaying information that might be used during the procedure itself, for example, via arrows 434 or gradations 232 as discussed below. The contrast agents may be incorporated into the supply tube 24 by a variety of known techniques, including, but not limited to, co-extrusion, assembly, pad printing, overmolding, etc.

Figure 3:
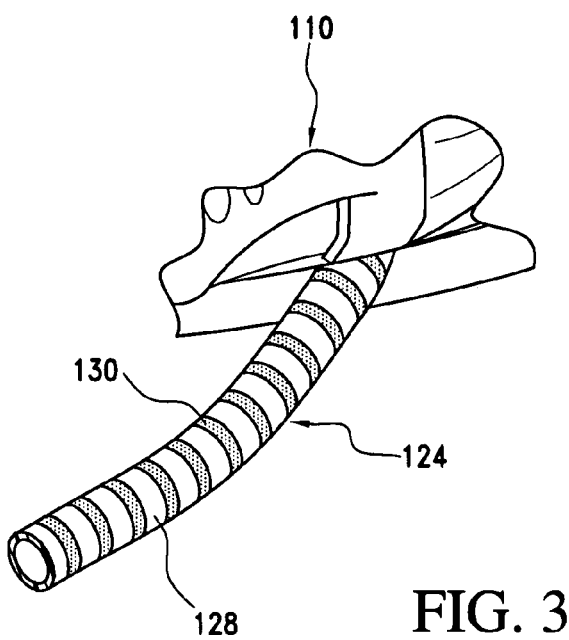

Similarly, and with reference to FIGS. 3, a gastric band 110 with clear sections 128 and radiopaque, white colored sections 130 functioning as a contrast mechanism is disclosed wherein the clear sections 128 and colored sections 130 are striped along the supply tube 124. Although multiple stripes 130 are disclosed in accordance with the embodiment shown in FIG. 3, it is contemplated one (or multiple) stripes 230 may be formed along the length of the supply tube 224 of a gastric band 210 as shown in FIG. 4.

In accordance with an alternate embodiment, and as shown in FIG. 5, the supply tube 324 of the gastric band 310 may have radiopaque, white colored gradations 332, which function as a contrast mechanism. In addition, to functioning as a contrast mechanism, these white colored gradations 332 would act as a ruler indicating to the surgeon either how much of supply tube he/she has cut off or how much is left adjacent the gastric band. As with the white colored sections disclosed with reference to FIGS. 1, 2, 3 and 4, the white colored gradations 332 are radiopaque for postoperative visualization purposes.

Figure 7:
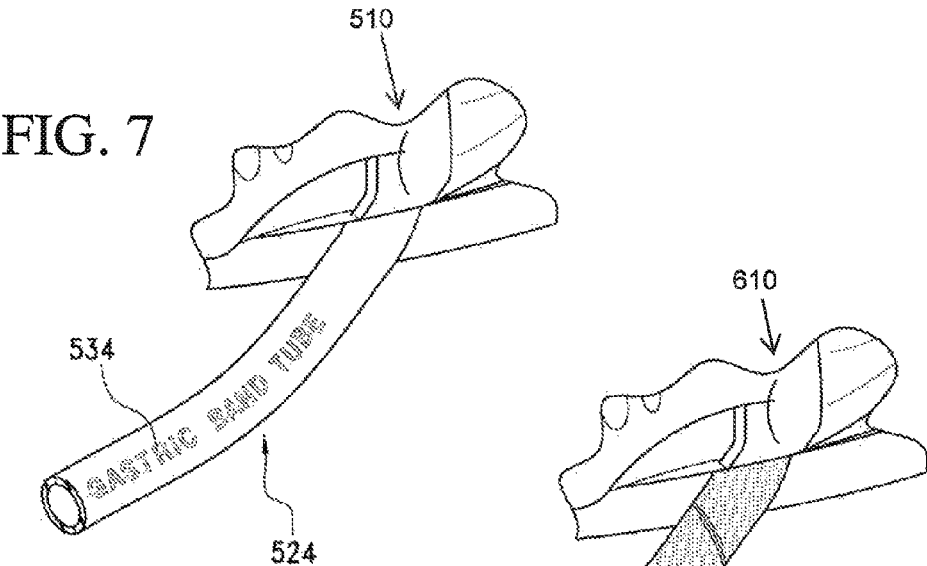

In addition to employing a combination of clear sections and white colored sections as shown above with reference to FIGS. 1, 2, 3, 4 and 5, the supply tube 424, 524 of the gastric band 410, 510 may also include contrast mechanisms composed of a third color of pad print 434 placed thereon (see FIGS. 6 and 7). The colored pad print 434, 534 includes, for example, arrows showing which direction the gastric band 510 or port is (see FIG. 6), or texts 534 such as the product name or instructions for the surgeon (see FIG. 7). In accordance with a preferred embodiment, the color pad prints 434, 534 are composed of non-radiopaque agents so as to provide for improved visualization during the procedure itself. For example, the main use of the arrows 434 and text 534 would be to show the surgeon where the end of the supply tube 424, 524 is and once the supply tube 424, 524 is attached to the fluid injection port, this function is no longer necessary. However, and as those skilled in the art will certainly appreciate, they could be composed of radiopaque agents without departing from the spirit of the present invention.

Figure 8:
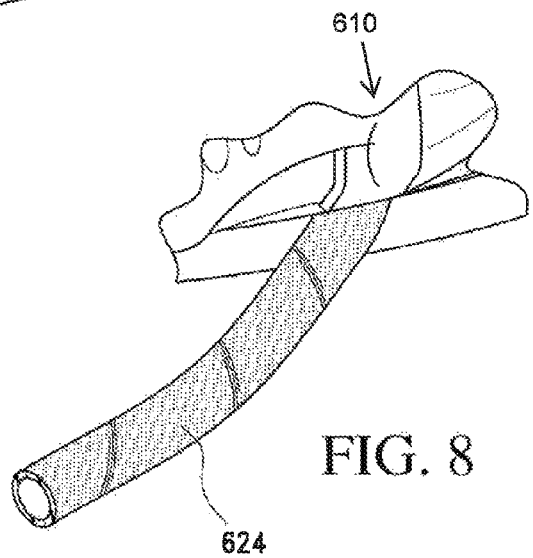

Although a supply tube with both clear sections and radiopaque, white colored sections is disclosed with reference to the various embodiment discussed above, the supply tube 624 of the gastric band 610 could be a milky color that is translucent as shown with reference to FIG. 8. It should be understood the term "milky color" is used in the present disclosure to describe a supply tube 624 providing both color (that is, a distinguishing pigment) while retaining the translucent qualities of the clear sections discussed above. The milky color of the supply tube 624 would be achieved by incorporating a contrast agent, such as, $BaSO_4$, $TiO_2$ or Ta into the material from which the supply tube 624 is composed. This would also allow for the incorporation of a radiopaque agent (for example, $BaSO_4$) allowing for it to be seen under an x-ray. In addition to $BaSO_4$, titanium dioxide or Ta could be utilized as a radiopaque agent. In accordance with a preferred embodiment, a very low percentage (>3%) of $BaSO_4$ is necessary to make the supply tube radiopaque. Such a low percentage is enough to give the supply tube 624 a white tint (i.e., milky), but not enough to make it white.

In addition to providing radiopaque agents allowing the supply tube to be seen under an x-ray, the white coloring incorporated within the tubing section therein could also be manufactured to permit visualization through devices such as an MRI.

Figure 9:
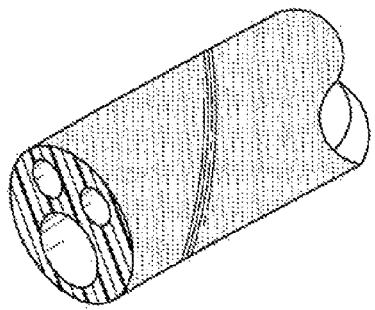
FIGS. 9 and 10 are cross sectional end views of various tube constructions which may be employed in accordance with the present invention.
Figure 10:
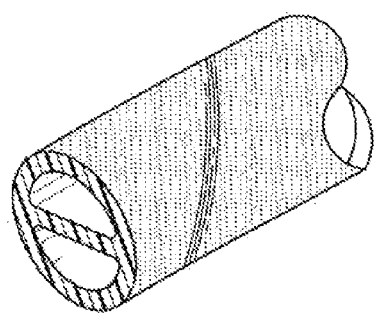

In addition, the supply tube may be multi-lumened or bifurcated (see FIGS. 9 and 10). As for the manufacturing of the tubing, it may be co-extruded, assembled or pad printed with white and clear materials. Although white is disclosed above in accordance with a preferred embodiment, different colors other than white or pad print black could be used in conjunction with the clear substrate and the tubing could be made out of many different materials, including, but not limited to silicone and various polymers.

Although the present invention is described for use in conjunction with gastric bands, those skilled in the art will appreciate the above invention has equal applicability to other types of implantable bands. For example, bands are used for the treatment of fecal incontinence. One such band is described in U.S. Pat. No. 6,461,292. Bands can also be used to treat urinary incontinence. One such band is described in U.S. Patent Application Publication No. 2003/0105385. Bands can also be used to treat heartburn and/or acid reflux. One such band is described in U.S. Pat. No. 6,470,892. Bands can also be used to treat impotence. One such band is described in U.S. Patent Application Publication No. 2003/0114729.

While the preferred embodiments have been shown and described, it will be understood that there is no intent to limit the invention by such disclosure, but rather, is intended to cover all modifications and alternate constructions falling within the spirit and scope of the invention.

The invention claimed is:
1. A balloon-type gastric band, comprising:
a balloon shaped and dimensioned to circumscribe a stomach at a predetermined location;
a supply tube secured to the balloon for fluid communication with an internal cavity of the balloon, wherein the supply tube includes both at least one radiopaque and colored section allowing for postoperative visualization by an external diagnostic tool and actual visualization and at least one clear section, which is transparent allowing a medical practitioner to check the supply tube, for respectively contrasting the supply tube from surrounding tissue when placed within a patient and facilitating identification of leaks within the supply tube.
2. The balloon-type gastric band according to claim 1, wherein the at least one radiopaque and colored section is an arrow.
3. The balloon-type gastric band according to claim 2, wherein the at least one radiopaque and colored section is text.
4. The balloon-type gastric band according to claim 1, wherein the at least one radiopaque and colored section includes gradations along a length of the supply tube.
5. The balloon-type gastric band according to claim 1, wherein the at least one radiopaque and colored section is spiraled.
6. balloon-type gastric band according to claim 1, wherein the at least one radiopaque and colored section is striped.
7. The balloon-type gastric band according to claim 6, wherein the at least one radiopaque and colored section is a circumferential stripe.

8. The balloon-type gastric band according to claim 6, wherein the at least one radiopaque and colored section is a longitudinal stripe.

9. The balloon-type gastric band according to claim 1, wherein the at least one radiopaque and colored section is a colored pad print.

10. The balloon-type gastric band according to claim 1, wherein the at least one radiopaque and colored section is composed of both radiopaque contrast agents and non-radiopaque contrast agents.

11. A balloon-type gastric band, comprising:
a balloon shaped and dimensioned to circumscribe a stomach at a predetermined location;
a supply tube secured to the balloon for fluid communication with an internal cavity of the balloon, wherein the supply tube is radiopaque and colored allowing for postoperative visualization by an external diagnostic tool and actual visualization while remaining translucent allowing a medical practitioner to check the supply tube.

12. The balloon-type gastric band according to claim 11, wherein the supply tube includes a contrast agent incorporated therein.

13. The balloon-type gastric band according to claim 11, wherein the contrast agent is radiopaque.

\* \* \* \* \*